(12) United States Patent
Van Steven-Daal et al.

(10) Patent No.: US 7,453,974 B2
(45) Date of Patent: Nov. 18, 2008

(54) BEAM-HARDENING AND ATTENUATION CORRECTION FOR COHERENT-SCATTER CT

(75) Inventors: Udo Van Steven-Daal, Aachen (DE); Jens-Peter Schlomka, Aachen (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 10/598,835

(22) PCT Filed: Mar. 15, 2005

(86) PCT No.: PCT/IB2005/050904

§ 371 (c)(1),
(2), (4) Date: Sep. 13, 2006

(87) PCT Pub. No.: WO2005/091225

PCT Pub. Date: Sep. 29, 2005

(65) Prior Publication Data

US 2007/0189444 A1    Aug. 16, 2007

(30) Foreign Application Priority Data

Mar. 17, 2004    (EP) .................................. 04101099

(51) Int. Cl.
    *H05G 1/60*    (2006.01)
(52) U.S. Cl. .......................................... 378/6; 378/207
(58) Field of Classification Search .............. 378/4, 378/6, 7, 207, 901
    See application file for complete search history.

(56) References Cited

U.S. PATENT DOCUMENTS 3,965,358 A * 6/1976 Macovski ...................... 378/5

4,149,081 A * 4/1979 Seppi ............................ 378/5

(Continued)

FOREIGN PATENT DOCUMENTS

DE    10252662 A1    5/2004

(Continued)

OTHER PUBLICATIONS

Schlomka et al., Novel Concept for Coherent Scatter X-ray Computed Tomography in Medical Applications, Penetrating Radiation Systems and Applications II, Proceedings of SPIE vol. 4142, pp. 218-224.*

(Continued)

*Primary Examiner*—Courtney Thomas
*Assistant Examiner*—Alexander H Taningco
(74) *Attorney, Agent, or Firm*—Michael E. Belk

(57) ABSTRACT

In CSCT, an exact reconstruction of a scattering function for each voxel is not known for polychromatic primary radiation. According to an exemplary embodiment of the present invention, a beam hardening compensation is performed prior to reconstruction allowing to perform a quasi-exact reconstruction on the basis of the primary radiation mean attenuation values are determined, from which an equivalent water thickness is derived. From the equivalent water thickness an energy shift is calculated, which is used to correct the initial mean energy of the scatter radiation. Furthermore, a CT reconstruction may be performed prior to a CSCT reconstruction allowing for a beam-hardening correction. Advantageously, this may allow for an improved image quality and an improved resolution of the scatter function.

14 Claims, 7 Drawing Sheets

| Primary Spectrum | Mean Energy @ 0 cm [keV] | Spectral width σ [keV] | Energy Shift [keV/cm] water/Lucite |
|---|---|---|---|
| 150 keV W, 1.5 mm Al filtered | 63.3 | 24.1 | 0.72/0.67 |
| 150 keV W, 1.5 mm Al+0.5 mm Cu | 77.1 | 23.7 | 0.49/0.45 |
| 150 keV W, 1.5 mm Al+1.0 mm Cu | 85.3 | 23.9 | 0.41/0.38 |
| 150 keV W, 1.5 mm Al+1.5 mm Cu | 91.6 | 23.5 | 0.35/0.32 |

U.S. PATENT DOCUMENTS

| | | | |
|---|---|---|---|
| 4,751,722 A | | 6/1988 | Harding et al. |
| 5,335,260 A | * | 8/1994 | Arnold .................. 378/207 |
| 5,602,895 A | * | 2/1997 | Fivez et al. .............. 378/98.4 |
| 6,075,877 A | * | 6/2000 | Takeo ..................... 382/130 |
| 6,157,703 A | * | 12/2000 | Solomon et al. ......... 378/158 |
| 6,320,931 B1 | * | 11/2001 | Arnold .................... 378/56 |
| 6,507,633 B1 | * | 1/2003 | Elbakri et al. ............. 378/8 |
| 7,065,234 B2 | * | 6/2006 | Du et al. .................. 382/131 |
| 7,248,726 B2 | * | 7/2007 | Sasada .................... 382/132 |
| 2002/0085671 A1 | * | 7/2002 | Sakaida ................ 378/98.11 |

FOREIGN PATENT DOCUMENTS

WO    WO2005091225 A1    9/2005

OTHER PUBLICATIONS

Nisar et al., Coherent Scatter X-ray Imaging of Plastic/Water Phantoms, Photonics North 2004: Photonic Applications in Astronomy, Biomedicine, Imgaging, Materials Processing, and Education, Proc. of SPIE vol. 5578, pp. 445-453.*

Schneider et al., Coherent Scatter Computed Tomography Applying a Fan-Beam Geometry, Medical Imgaing 2001: Physics of Medical Imaging, Proceedings of SPIE vol. 4320, pp. 754-763.*

Casteele et al., An Energy-based Beam Hardening Model in Tomography, Physics in Medicine and Biology, Institute of Physics Publishing, 47, 2002, pp. 4181-4190.*

Schlomka et al., Novel Concept for Coherent Scatter X-ray Computed Tomography in Medical Applications, Penetrating Radiation Systems and Applications II, Proceedings of SPIE vol. 4142, 2000, pp. 218-224.*

Nisar et al., Coherent Scatter X-ray Imaging of Plastic/Water Phantoms, Photonics North 2004: Photonic Applications in Astronomy, Biomedicine, Imgaging, Materials Processing, and Education, Proc. of SPIE vol. 5578, 2004, pp. 445-453.*

☐☐Schneider et al., Coherent Scatter Computed Tomography Applying a Fan-Beam Geometry, Medical Imgaing 2001: Physics of Medical Imaging, Proceedings of SPIE vol. 4320, 2001, pp. 754-763.*

Gerhard Martens et al: "Coherent X-ray Scatter Imaging for Foodstuff Contamination Detection"; Proc SPIE In. Soc. Opt Eng;Proceedings of SPIE-The Intl Society for Optical Engineering 1194 Publ. by Society of Photo-Optical Instrumentation Engineers, Bellingham, WA, USA, vol. 2092, Oct. 3, 1993, pp. 387-398, XP002328194.

Schneider S. M. et al: Coherent Scatter Computed Tomography Applying a Fan-Beam Geometry:; Proceedings of the SPIE, Bellingham, WA, US; vol. 4320, Feb. 18, 2001; pp. 754-763, XP008004551.

McDavid W. D. et al: "Correction for Spectral Artifacts in Cross-Sectional Reconstruction From X-Rays." vol. 4, No. 1, Jan. 1977; pp. 54-57, XP002328195.

Harding G. et al: "Energy-Dispersive X-ray Diffraction Tomography"; Phys. Med. Biol., 1990, vol. 35, No. 1 33-41.

Katsevich: "Analysis of an Exact Inversion Algorithm for Spiral Cone-Beam CT"; Phys. Med. Biol., vol. 47, pp. 2583-2597, 2002.

Patch S. K.: "Computation of Unmeasured Third-Generation VCT Views From Measured View"; IEEE Trans. Med. Img. MI-21, pp. 801-813, Jul. 2002.

Defrise, M. et al: "Improved 2D Rebinning of Helical Cone-Beam CT Data Using John's Equation"; Proc. 2002 IEEE Nuclear Scinece and Medical Imaging Symposium, Norfolk, VA; Paper M10-74.

* cited by examiner

| Primary Spectrum | Mean Energy @ 0 cm [keV] | Spectral width σ [keV] | Energy Shift [keV/cm] water/Lucite |
|---|---|---|---|
| 150 keV W, 1.5 mm Al filtered | 63.3 | 24.1 | 0.72/0.67 |
| 150 keV W, 1.5 mm Al+0.5 mm Cu | 77.1 | 23.7 | 0.49/0.45 |
| 150 keV W, 1.5 mm Al+1.0 mm Cu | 85.3 | 23.9 | 0.41/0.38 |
| 150 keV W, 1.5 mm Al+1.5 mm Cu | 91.6 | 23.5 | 0.35/0.32 |

BEAM-HARDENING AND ATTENUATION CORRECTION FOR COHERENT-SCATTER CT

The present invention relates to the field of coherent-scatter computed tomography (CSCT), where a fan-beam is applied to an object of interest. In particular, the present invention relates to a method of reconstructing coherent-scatter computed tomography data of an object of interest, to a coherent-scatter computed tomography apparatus, to a data processing device for reconstructing coherent-scatter computed tomography data and to a computer program for reconstructing coherent-scatter computed tomography data.

U.S. Pat. No. 4,751,722 describes a device based on the principle of registration of an angled distribution of coherent scattered radiation within angles of 1° to 12° as related to the direction of the beam. As set forth in the U.S. Pat. No. 4,751,722, the main fraction of elastic scattered radiation is concentrated within angles of less than 12° for photon energies >40 keV, and the scattered radiation has a characteristic angle dependency with well marked maxima, the positions of which are determined by the irradiated substance itself. As the distribution of the intensity of the coherently scattered radiation in small angles depends on the molecular structure of the substance, different substances having equal absorption capacity (which cannot be differentiated with conventional transillumination or CT) can be distinguished according to the distribution of the intensity of the angled scattering of coherent radiation typical for each substance.

Due to the improved capabilities of such systems to distinguish different object materials, such systems find more and more application in medical or industrial fields.

The dominant component of low-angle scatter is coherent scatter. Because coherent scatter exhibits interference effects which depend on the atomic arrangement of the scattering sample, coherent scatter computer tomography (CSCT) is in principle a sensitive technique for imaging spatial variations in the molecular structure of tissues or other materials across a 2D object section.

Harding et al. "Energy-dispersive x-ray diffraction tomography" Phys. Med. Biol., 1990, Vol. 35, No. 1, 33-41 describes an energy dispersive x-ray diffraction tomograph (EXDT) which is a tomographic imaging technique based on an energy analysis at fixed angle, of coherent x-ray scatter excited in an object by polychromatic radiation. According to this method, a radiation beam is created by the use of suitable aperture systems, which has the form of a pencil and thus is also referred to as a pencil beam. Opposite to the pencil beam source, one detector element suitable for an energy analysis is arranged for detecting the pencil beam altered by the object of interest.

Due to the use of the pencil beam in combination with only one detector element, only a limited number of photons emitted by the source of radiation and thus only a reduced amount of information can be measured. In case EXDT is applied to larger objects such as for example to pieces of baggage, EXDT has to be used in a scanning mode thus causing extremely long measurement times.

A coherent scatter set-up applying a fan-beam primary beam and a 2D detector in combination with CT was described in U.S. Pat. No. 6,470,067 B1 thus overcoming the long measurement time involved in EXDT scanning mode. The shortcoming of the angle-dispersive set-up in combination with a polychromatic source are blurred scatter functions, which is described in e.g. Schneider et al. "Coherent Scatter Computer Tomography Applying a Fan-Beam Geometry" Proc. SPIE, 2001, Vol. 4320 754-763.

In today's CT scanners, usually polychromatic x-ray sources are used as radiation sources. No exact reconstruction of a scattering function for a voxel is known for polychromatic primary radiation as emitted from such polychromatic x-ray sources.

It is an object of the present invention to provide for an improved reconstruction of coherent-scatter computed tomography data.

According to an exemplary embodiment of the present invention, the above object may be solved by a method of reconstructing coherent-scatter computed tomography (CSCT) data of an object of interest wherein attenuation data of the object of interest is acquired from primary radiation transmitted through the object of interest. Then, a compensation of scatter radiation data is performed on the basis of the acquired attenuation data. The scatter radiation data is based on scatter radiation scattered from the object of interest. The coherent-scatter computed tomography data is then reconstructed by using the compensated scatter radiation data. According to an aspect of this exemplary embodiment of the present invention, a beam-hardening compensation of the scatter radiation data is performed.

According to this exemplary embodiment of the present invention, it has been found that a scattering angle for a given momentum transfer depends on the energy of the scattered photon and the signal structure measured on the respective scatter radiation detector is then a function of superimposed scatter projections for the different energies weighted with the intensity and the energy-dependent attenuation. When images are reconstructed from polychromatic projection, i.e. projections taken with a polychromatic source of radiation, an average energy of the spectrum may be used and then, a monochromatic reconstruction may be applied by using this average energy. However, this may cause a smearing of the scatter function due to the spectrum distribution of the primary radiation.

According to the exemplary embodiment of the present invention as set forth above, the scatter radiation data is compensated for beam-hardening effects. This may reduce a smearing of the reconstructed scatter function. Furthermore, this may enable a quasi-exact determination of the back-projection paths by taking into account the beam-hardening effect.

According to another exemplary embodiment of the present invention, a compensation of a beam-hardening effect is performed on the basis of an energy shift determined on the basis of an equivalent object. The energy shift caused by the beam-hardening effect of this equivalent object is known and may be used for compensation. This may allow for an improved image quality.

According to another exemplary embodiment of the present invention, a mean attenuation caused by the object of interest is determined on the basis of the attenuation data. Then, an equivalent thickness of a pre-selected material such as water and/or any other proper material, e.g. PMMA, is determined on the basis of the mean attenuation. On the basis of the equivalent thickness an energy shift is determined which is then used for compensating the scatter radiation data.

In other words, according to this exemplary embodiment of the present invention, an energy-dependent attenuation correction (beam-hardening correction) is performed. According to an aspect of this exemplary embodiment, this energy-dependent attenuation correction may be performed prior to the reconstruction.

Advantageously, this may allow for a very good spectral resolution of reconstructed scatter functions. For example, in material discrimination applications, this may allow to discriminate materials having the same attenuation. Also, due to the attenuation correction, an improved image quality may be obtained.

According to another exemplary embodiment of the present invention, a reconstruction of a volume data set comprising absorption coefficients of the object of interest is performed. Then, radiation spectra are determined for scattered photons of the scatter radiation. Mean energies of the scattered photons are determined on the basis of the radiation spectra and then a reconstruction of the coherent-scatter computed tomography data is performed by using these mean energies.

In other words, according to this exemplary embodiment of the present invention, a CT reconstruction is performed prior to the CSCT reconstruction. This advantageously allows for a quasi-exact calculation of the back-projection path (of materials occurring on these paths) by taking into account, for example, the beam-hardening effect on the average energy of the scattered photons.

According to another exemplary embodiment of the present invention, on the basis of the attenuation data, a material is determined located on a path of a scattered photon of the scatter radiation. This is done on the basis of the CT reconstruction. Then, for performing a correction or compensation of the scatter radiation data, these materials are taken into account and beam-hardening effects and/or absorption effects may be compensated for in the scatter radiation data. A CSCT reconstruction is then performed on the basis of the corrected scatter radiation data.

According to another exemplary embodiment of the present invention, a coherent-scatter computed tomography apparatus is provided where a beam-hardening compensation of scatter radiation data is performed. Advantageously, this coherent-scatter computed tomography apparatus may be part of a cone-beam CT system. Due to the described reconstruction according to the present invention which may allow for an improved image quality, this apparatus may advantageously be used in medical imaging for material analysis and, for example, for baggage inspection. Advantageously, for these applications a good resolution of the scatter function which may be achieved with the apparatus according to the present invention is important.

According to another exemplary embodiment of the present invention, a data processing device is provided comprising a memory and a data processor. The data processing device according to this exemplary embodiment is adapted to perform the method of the present invention.

According to another exemplary embodiment of the present invention, a software program for reconstructing coherent-scatter computed tomography data of an object of interest is provided wherein, when the computer software is executed on one of the data processor and a coherent-scatter computed tomography apparatus, an operation in accordance with the method of the present invention is performed. The computer program according to the present invention may be stored on a computer readable medium, such as a CD-ROM. The computer program may also be presented over a network such as the WorldWideWeb and may be downloaded into the working memory of a data processor from such a network. The computer program may be written in any suitable programming language, such as C++.

It may be seen as a gist of an exemplary embodiment of the present invention that a beam-hardening compensation is performed on the scatter radiation data before the scatter radiation data is used for reconstruction. This may allow for a very good spectral resolution of reconstructed scatter functions and may allow to obtain an improved image quality.

These and other aspects of the present invention are apparent from and will be elucidated with reference to the embodiments described hereinafter and with reference to the following drawings.

In the following description of FIGS. 1-13, the same reference numerals will be used for the same or corresponding elements.

Figure 1:
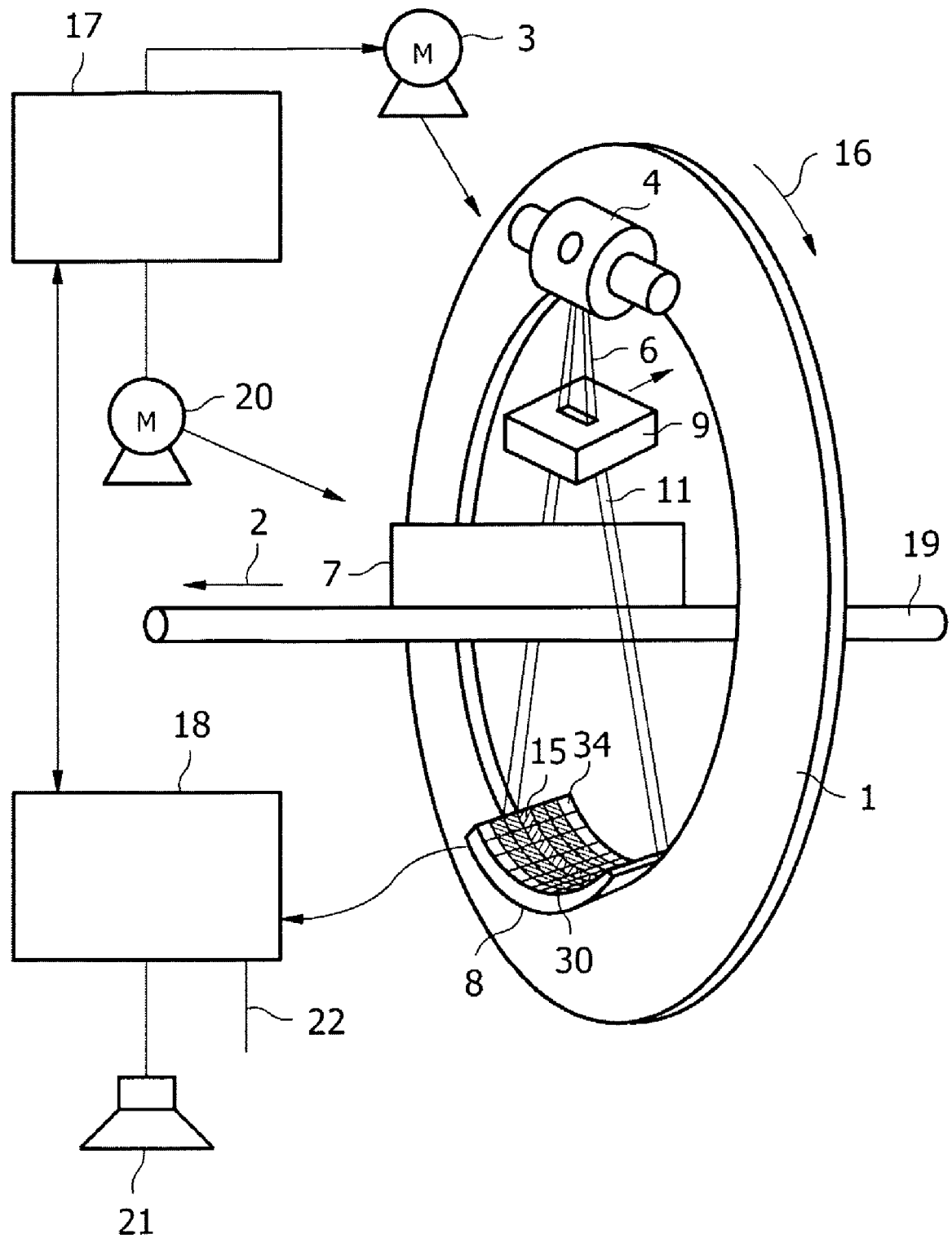
FIG. 1 shows a schematic representation of an exemplary embodiment of a computer-tomograph according to the present invention.

FIG. 1 shows an exemplary embodiment of a computer-tomograph according to the present invention. With reference to this exemplary embodiment, the present invention will be described for the application in baggage inspection, for example to detect hazardous materials, such as explosives, in items of baggage. However, it has to be noted that the present invention is not limited to the fields of baggage inspection, but can also be used in other industrial or medical applications, such as, for example, in bone imaging or discrimination of tissue types in medical applications. Also, the present invention may be used in the field of non-destructive testing.

The computer-tomograph depicted in FIG. 1 comprises a gantry 1, which is rotatable around a rotational axis 2. The gantry 1 is driven by means of a motor 3. Reference character 4 designates the source of radiation, such as an x-ray source which, according to an aspect of the present invention, emits polychromatic or monochromatic radiation.

Reference numeral 9 designates a collimator, e.g. a slit diaphragm. The fan plane or scan plane of fan beam 11 penetrating through the object of interest 7 intersects a transmission detector line 15 of the radiation detector 8.

In other words, the fan beam 11 is directed such that it penetrates the item of baggage 7 arranged in the center of the gantry 1, i.e. in an examination region of the computer-tomograph, and impinges onto the detector 8. As described above, the detector 8 is arranged on the gantry 1 opposite to the radiation source 4 such that the fan plane of the fan beam 11 intersects the row or line 15 of the detector 8. The detector 8 is depicted in FIG. 1 as having seven detector lines, each comprising a plurality of detector elements. As mentioned above, the detector 8 is arranged such that the primary radiation detector 15, i.e. the middle line of the detector 8, is in the fan plane of the fan beam 11.

The remaining six lines of the detector 8, i.e. the three detector lines 30 and 34 on each side of the detector line 15 indicated with hatching, are scatter radiation detector lines. Such detector lines 30 and 34 are respectively arranged outside of the fan plane of the fan beam 11. In other words, those lines 30 and 34 are arranged at the gantry 1 opposite to the x-ray source 4 with an offset from the fan plane in a direction parallel to the rotational axis 2 or in a direction normal to the fan plane. The detector line 30 is arranged with a positive offset with respect to the direction of the rotational axis 2 depicted in FIG. 1 whereas the line 34 is arranged with a negative offset from the fan plane with respect to the direction of the rotational axis 2 depicted in FIG. 1.

The detector lines 30 and 34 are arranged at the gantry 1 such that they are parallel to the fan plane and out of the fan plane with such an offset in a positive or negative direction of the rotational axis 2 of the gantry 1 such that they receive or measure a scatter radiation scattered from the item of baggage 7 in the examination area of the computer-tomograph. Thus, in the following, lines 30 and 34 will also be referred to as scatter radiation detector.

The detector elements of the detector lines 15, 30 and 34 may be scintillator detector cells. However, according to a variant of this exemplary embodiment of the present invention cadmium telluride or CdZnTe based or other direct-conversion detector cells may be used for either line 15 or line 34 or 30. Also, lines 30 and 34 may be cadmium telluride or CZT based detector cells and the line 15 may be a line of a scintillator detector cell. The primary beam detectors and the scatter radiation detectors may be placed in separate housings.

It has to be noted that the provision of only one line 30 or 34 may be sufficient. However, preferably a plurality of lines 30 and/or 34 is provided. Also, the provision of only one line 15 measuring the attenuation caused by the item of baggage 7 of the primary beam of the fan beam 11 in the fan plane may be sufficient. However, as in the case of the lines 30 and 34, a provision of a plurality of detector lines 15 may further increase the measurement speed of the computer-tomograph. In the following, the term "primary radiation detector" will be used to refer to a detector, including at least one detector line for measuring an attenuation of the primary radiation of the fan beam 11.

As may be taken from FIG. 1, the detector cells of the detector 8 are arranged in lines and columns, wherein the columns are parallel to the rotational axis 2, wherein the lines are arranged in planes perpendicular to the rotational axis 2 and parallel to the slice plane of the fan beam 11.

During a scan of the item of baggage 7, the radiation source 4, the collimator 9 (or an aperture system) and the detector 8 are rotated along the gantry 1 in the direction indicated by arrow 16. For rotation of the gantry 1 the motor 3 is connected to a motor control unit 17, which is connected to a calculation unit 18.

In FIG. 1, the item of baggage 7 is disposed on a conveyor belt 19. During the scan of the item of baggage 7, while the gantry 1 rotates around the item of baggage 7, the conveyor belt 19 displaces the item of baggage 7 along a direction parallel to the rotational axis 2 of the gantry 1. By this, the item of baggage 7 is scanned along a helical scan path. The conveyor belt 19 can also be stopped during the scans to thereby measure single slices.

The detector 8 is connected to a calculation unit 18. The calculation unit 18 receives the detection results, i.e. the readouts from the detector elements of the detector 8, and determines a scanning result on the basis of the scanning results from the detector 8, i.e. from the scatter-detector lines 30 and 34 and the line 15 for measuring the attenuation of the primary radiation of the fan-beam 11. In addition to that, the calculation unit 18 communicates with the motor control unit 17 in order to coordinate the movement of the gantry 1 with the motors 3 and 20 or with the conveyor belt 19.

The calculation unit 18 is adapted for reconstructing an image from readouts of the primary radiation detector, i.e. detector line 15 and the scatter radiation detector, i.e. lines 30 and 34. The image generated by the calculation unit 18 may be output to a display (not shown in FIG. 1) via an interface 22.

Furthermore, the calculation unit 18 is adapted for the detection of explosives in the item of baggage 7 on the basis of the readouts of the lines 30 and 34 and 15. This can be made automatically by reconstructing scatter functions from the readouts of these detector lines and comparing them to tables including characteristic measurement values of explosives determined during preceding measurements. In case the calculation unit 18 determines that the measurement values read out from the detector 8 match with characteristic measurement values of an explosive, the calculation unit 18 automatically outputs an alarm via a loudspeaker 21.

Figure 2:
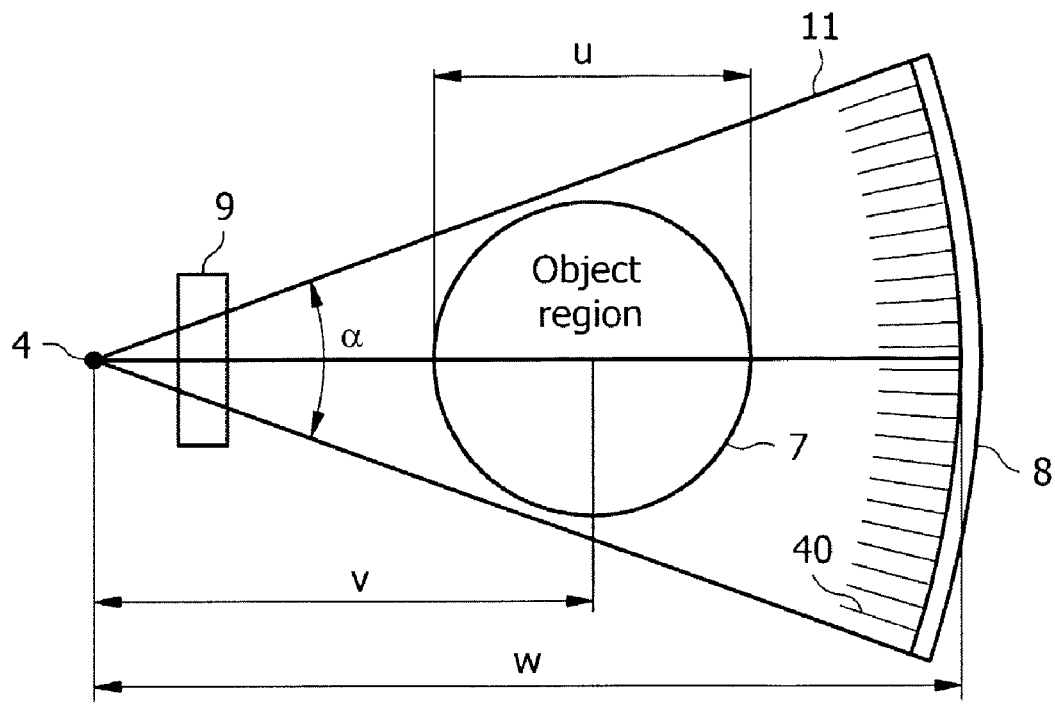
FIG. 2 shows a schematic representation of a geometry of the computer-tomograph of FIG. 1 for the measurement of coherent scatter radiation.

FIG. 2 shows a simplified schematic representation of a geometry of the CSCT scanning system depicted in FIG. 1. As may be taken from FIG. 2, the x-ray source 4 emits the fan-beam 11 such that it includes the item of baggage 7 in this case having a diameter of u and covers the entire detector 8. The diameter of the object region may, for example, be 100 cm. In this case, an angle α of the fan-beam 11 may be 80°. In such an arrangement, a distance v from the x-ray source 4 to the center of the object region is approximately 80 cm and the distance of the detector 8, i.e. of the individual detector cells from the x-ray source 4, is approximately w=150 cm.

As can be taken from FIG. 2, according to an aspect of the present invention, the detector cells or lines can be provided with collimators 40 to avoid that the cells or lines measure unwanted radiation having a different scatter angle. The collimators 40 have the form of blades or lamellas, which can be focused towards the source. The spacing of the lamellas can be chosen independently from the spacing of the detector elements.

Instead of a bent detector 8 as depicted in FIGS. 1 and 2, it is also possible to use a flat detector array.

Figure 3:
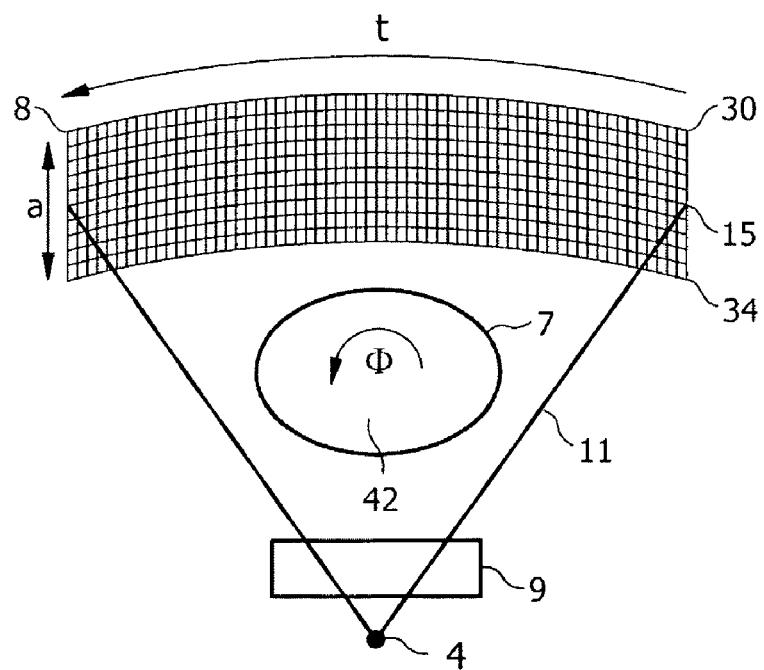
FIG. 3 shows another schematic representation of the geometry of the computer-tomograph of FIG. 1.

FIG. 3 shows another schematic representation of a detector geometry as used in the computer tomograph of FIG. 1. As already described with reference to FIG. 1, the detector 8 may comprise one, two or more detector lines 30 and 34 and a plurality of lines 15 for measuring the attenuation of the primary fan-beam caused by the item of baggage 7. As may be taken from FIG. 3, preferably the detector 8 is arranged such that the middle line 15 of the detector 8, is within the fan plane of the fan-beam 11 and thereby measures the attenuation in the primary radiation. As indicated by arrow 42, the radiation source of x-ray source 4 and the detector 8 are rotated together around the item of baggage to acquire projections from different angles.

As depicted in FIG. 3, the detector 8 comprises a plurality of columns t.

Figure 4:
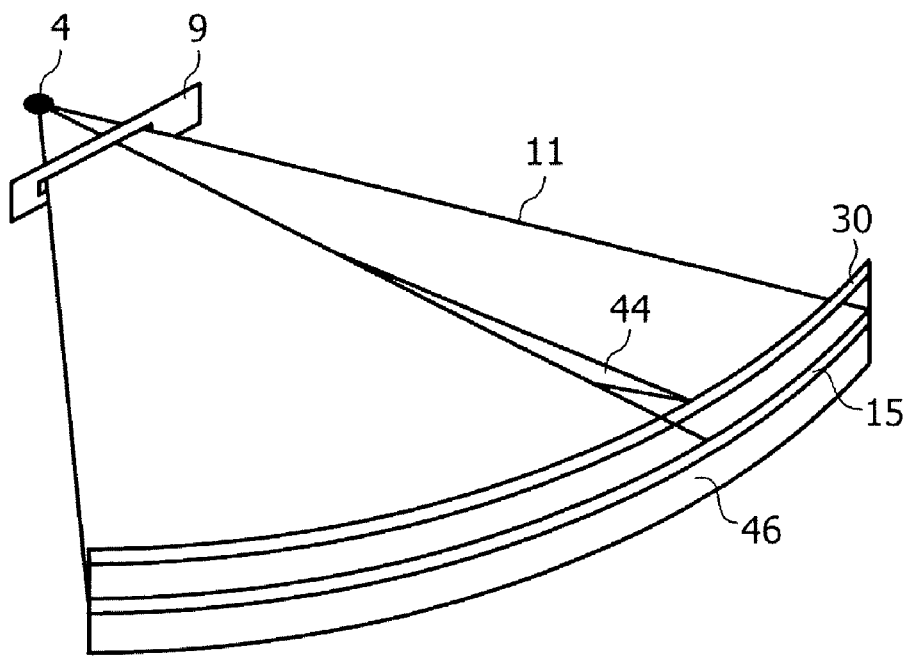
FIG. 4 shows another schematic representation of a measurement geometry of the computer-tomograph of FIG. 1 for further explaining the present invention.

FIG. 4 shows another schematic representation of the geometry of the computer tomograph depicted in FIG. 1 for further explaining the present invention. In FIG. 4, a detector 46 is depicted, comprising only one line 15 and only one line 30. The line 15 is arranged in the fan plane of the fan-beam 11 formed by the collimator 9. The line 15 comprises, for example, scintillator cells or other suitable cells for measuring the attenuation of the primary beam of the fan-beam 11 and allows for an integral measurement of the attenuation of the primary fan-beam caused by the object of interest in the object region or examination region.

Line 30 depicted in FIG. 4 may include energy resolving cells or scintillator cells. As may be taken from FIG. 4, the line 30 is arranged parallel to the fan plane of the fan-beam 11 but out of the plane. In other words, the line 30 is arranged in a plane parallel to the fan plane and parallel to the line 15. The fan plane may also be referred to as slice plane.

Reference numeral 44 indicates a scatter radiation, i.e. a photon scattered by the object of interest, such as the item of baggage. As may be taken from FIG. 4, the scatter radiation leaves the slice plane and impinges onto a detector cell of the line 30.

Figure 5:
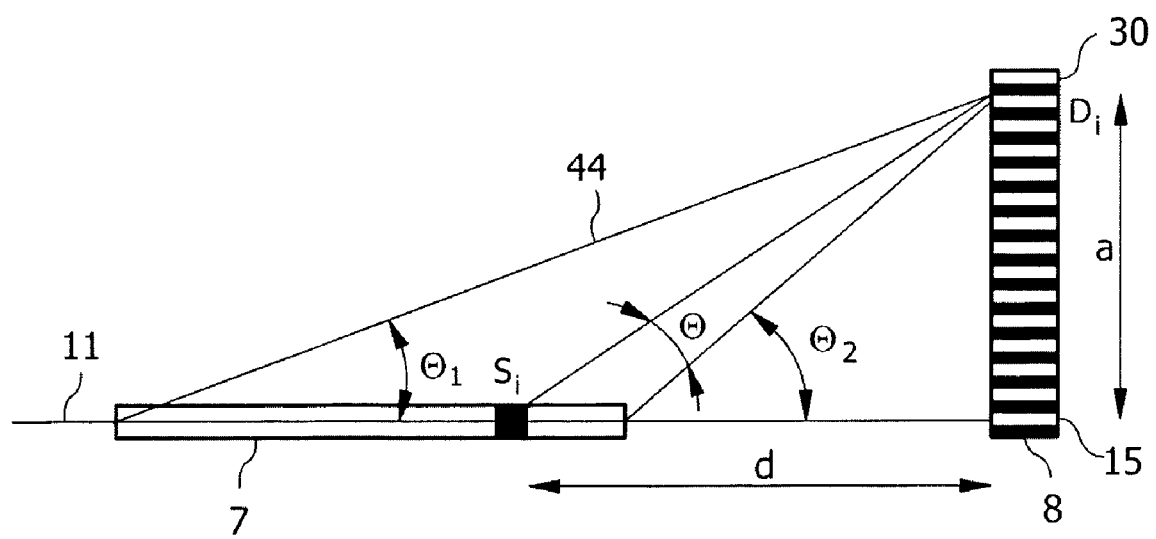
FIG. 5 shows another schematic representation of a side view of the geometry of the computer-tomograph of FIG. 1.

FIG. 5 shows a side view of the detector geometry of the computer tomograph of FIG. 1. FIG. 5 can also be contemplated as showing a side view of FIG. 4, where, however, instead only the provision of one line 30 and one line 15, in FIG. 5 there is provided a plurality of detector lines between the line 30 and the line 15. The detector element $D_i$ is arranged with a fixed distance a from the slice plane of the primary fan-beam. According to an aspect of the present invention, for each detector element $D_i$ of the column t and for each projection $\Phi$ (see FIG. 3) a spectrum I (E, t, $\Phi$) is measured. Performing this measurement for a plurality of projections $\Phi$ along a circular or helical scan path, a three-dimensional data set is acquired. Each object pixel is described by three coordinates (x, y, q). Thus, according to an aspect of the present invention, for reconstructing an image or for reconstructing further information from the three-dimensional data set, a 3D→3D reconstruction method is applied such as the one described in DE 10252662.1, which is hereby incorporated by reference.

Figure 6:
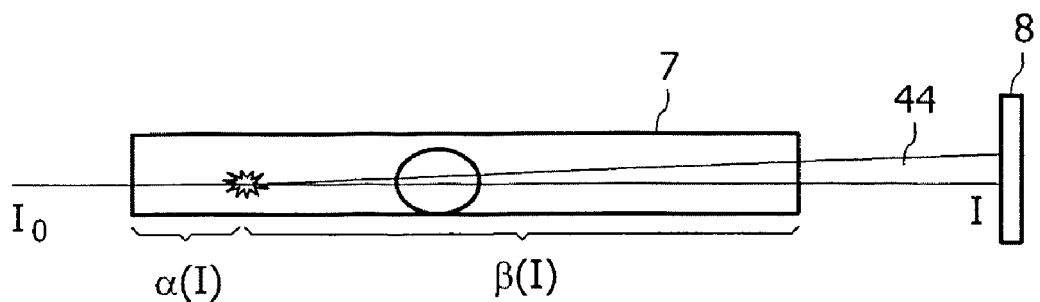
FIG. 6 shows another schematic representation for further explaining a scatter event occurring in the computer-tomograph of FIG. 1.

FIG. 6 shows a schematic representation for explaining a scatter event occurring in the object of interest. The intensity I at the detector 8 may be determined from the following equation:

$$I = \int_{E_{min}}^{E_{max}} I_0(E)\alpha(E)F^2(q, E)\beta(E)dE, \quad \text{(equation 3)}$$

From equation 3 it may be taken that the detector signal I at a detector 8 is a superposition of scattered projections for a variety of energies which are weighted with the intensity $I_0(E)$ and the attenuation which is dependent on the energy. F is the scatter function. The attenuation factors $\alpha(E)$ and $\beta(E)$ describe the attenuation of the incoming radiation along the path from the source to the location of the scatter event and from the location of the scatter event to the detector.

A simple approach for reconstructing images from the projection data which has been determined on the basis of polychromatic radiation is to calculate a mean energy of the spectrum and then to perform a "monochromatic" reconstruction. However, as indicated above, this may cause a smearing of the scattered function in dependence of the wave vector transfer in the reconstructed images caused by the spectral nature of the primary radiation.

According to exemplary embodiments of the present invention which will be described in further detail with reference to FIGS. 10 and 11, methods are provided wherein the polychromatic nature, and by this the beam-hardening of the primary radiation, is contemplated for the determination of the back-projection paths. This may allow for a quasi-polychromatic reconstruction.

Figure 7:
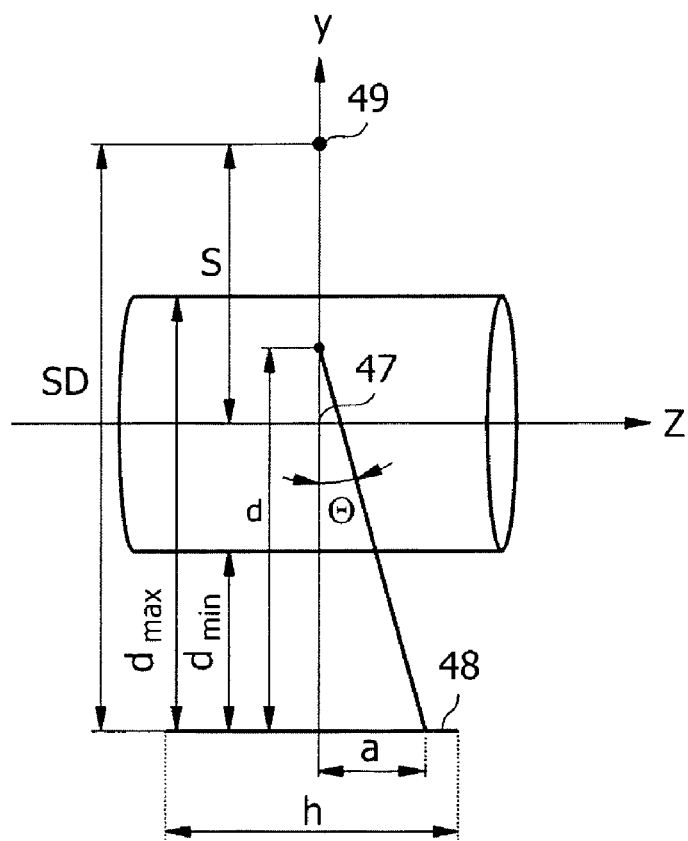
FIG. 7 shows a schematic representation of a multi-line CSCT scanner according to another exemplary embodiment of the present invention.

FIG. 7 shows a schematic drawing of an exemplary embodiment of a multi-line CSCT scanner. This scanner is provided with a detector 48, comprising a plurality of lines of energy resolving detector elements, which may be the same as the ones described with reference to FIG. 1. The source of radiation 9 is provided with collimators, such that it generates a fan-beam of x-rays. The arrangement of the detector 48 and the source of radiation 49 is such that the detector 48 is focus centered. The view depicted in FIG. 6 is parallel to the scanned plane or slice plane in order to further clarify the scanning process out of the x-y plane, i.e. the rotation plane of the source of radiation 49 and the detector 48. As may be taken from FIG. 6, a distance between the source of radiation 49 and the detector 48 is indicated as "SD", a distance between the source 49 and the center of rotation 47 is indicated by S, a distance between the scatter center and the detector 48 is indicated by d, a distance between a detector element receiving radiation, the scanned plane or sliced plane is indicated by a and h indicates a height of the detector 48.

The z coordinate axis is a normal on the center of the rotation plane of the source of radiation 49, i.e. the axis of rotation of the source of radiation 49. The y coordinate is in the rotation plane of the source of radiation.

As may be taken from FIG. 7, for the following description, a CSCT scanner with, for example, a polychromatic x-ray source 49 and a detector 48 is considered. The detector comprises or consists of energy resolving detector elements, which may be similar to the ones described with reference to FIG. 1. The emitted x-rays have been collimated, such that a fan-beam radiates the object of interest located in an area around the center of radiation 47.

The following method of operation may be applied in the above scanner, or in the scanner described with reference to FIG. 1, for reconstructing the CSCT data, i.e. for reconstructing an image from the read-outs of the detectors 8 and 48.

Step 1: The data is measured during a circular acquisition referring to the source trajectory in the x-y-z space. In other words, read-outs are gathered from detectors 8 or 48, while the source of radiations 4 and 49 and the detectors 8 and 48 are rotated around the object of interest in a rotational plane. The read-outs are referred to as measured data or acquired CSCT data. The measured CSCT data is interpreted as line integrals in the x-y-q space, where q represents the wave-vector transfers. The calculation of the wave-vector transfers will be described later on.

Step 2: The acquired CSCT data is resorted and extrapolated, such that it corresponds to an acquisition along a helical trajectory in the x-y-q space.

Step 3: A further step may be performed in order to pre-process the data according to conventional helical reconstruction algorithms, such as, for example, the exact reconstruction technique described by Katsevich "Analysis of an exact inversion algorithm for spiral cone-beam CT", Phys. Med. Biol., vol. 47, p. 2583-2597, 2002, which is hereby incorporated by reference.

Step 4: Then, the resorted and/or extrapolated data may be back projected. This back-projection may be performed along the curved lines in the x-y-q space. These curved lines may, for example, be hyperbolas.

This operation, in particular step 2, will be described in more detail in the following:

CSCT makes use of coherently scattered x-rays, in order to reconstruct the coherent scatter form factor $F^2(q)$. The differential cross-section for coherently scattered x-rays $d\sigma_{Rayleigh}/d\Omega$ is given by $$\frac{d\sigma_{Rayleigh}}{d\Omega} = \frac{1}{2}r_e^2(1+\cos^2\Theta)F^2(q), \quad \text{(equation 4)}$$

where $r_e$ denotes the classical electron radius, and $\Theta$ the angle between the incoming and the scattered x-rays. The wave-vector transfer q causing the deviation of the photon by the angle $\Theta$ is defined by $$q = \frac{E}{hc}\sin(\Theta/2), \quad \text{(equation 5)}$$

with the energy E of the corresponding x-ray photon, Planck's constant h and the speed of light c. For scattering under small angles, e.g. the angle regime of interest here is between 0 and 6°, $\sin(\Theta/2)$ can be approximated by $\Theta/2$, and Eq.(5) can be written as $$q \approx \frac{E}{hc}\frac{\Theta}{2}. \quad \text{(equation 6)}$$

According to FIG. 6, the scatter angle is given by the distance d of the scatter center from the detector and the distance a of the detector element which receives the scattered radiation from the scanning plane:

$$\tan\Theta \approx \Theta = \frac{a}{d}. \quad \text{(equation 7)}$$

Together with Eq. (6), this yields:

$$q = \frac{E}{hc}\frac{a}{2d}. \quad \text{(equation 8)}$$

The x-y-q space, Eq. (8) describes hyperbolas. These hyperbolas can be approximated by straight lines. Among several possibilities is, for example, an approximation such that the area under a straight line matches the area of the corresponding hyperbola. Another approximation is described here. The straight line intersects the hyperbola at the beginning ($d_{max}$) and at the end ($d_{min}$) of the region of interest:

$$q = \frac{1}{2hc}\left[\frac{d_{min}+d_{max}-d}{d_{min}\times d_{max}}\right]aE. \quad \text{(equation 9)}$$

Figures 8, 9:
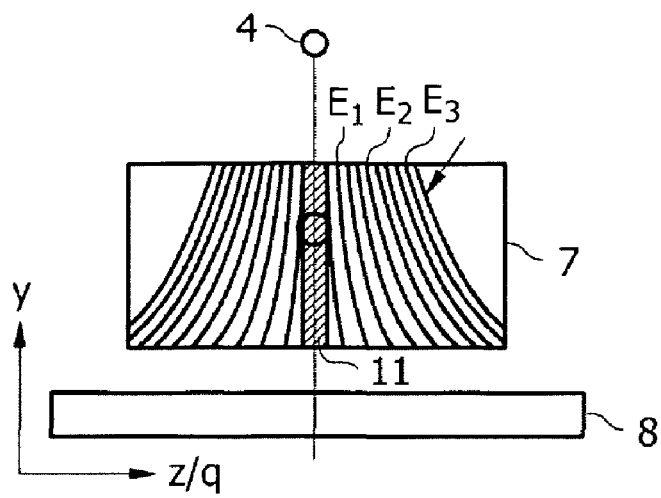
FIG. 8 shows back-projection paths used for performing a back-projection according to an exemplary embodiment of the present invention.
FIG. 9 shows a table used for determining an energy shift according to an exemplary embodiment of the present invention.

FIG. 8 shows such hyperbolas. In detail, FIG. 8 shows a back-projection path as determined by creation 8. As may be taken from FIG. 8, for each mean energy, a new path is obtained.

A scanning system is considered, such as the ones depicted in FIGS. 1 and 6, where the real path can be resorted and extrapolated such that it corresponds to an acquisition along a helical trajectory in the x-y-q space. The extrapolation of the data measured on a circular trajectory to virtual neighboring trajectories is done by using John's Equation. The idea of John's Equation is that the space of line integrals through 3D space is 4D, thus the mapping from object function to its line integral function creates an additional dimension, as described in S. K. Patch, "Consistency conditions upon 3D CT data and the wave equation", Phys. Med. Biol. 47, 2637-2650. U.S. Pat. No. 6,173,030 (1999), which is hereby incorporated by reference.

Line integrals for the virtual source position $\tilde{q}$ may be extrapolated from the line integrals measured for source positions for $\tilde{q}=0$.

This implies redundancy in line integral space, which is then used to construct unmeasured from measured data as described in S. K. Patch "Computation of unmeasured third-generation VCT views from measured views", IEEE Trans. Med. Img. MI-21, 801-813. U.S. Pat. No. 6,292,526 (1999), which is hereby incorporated by reference. John's Equation is parametrized as follows for the set of geometry parameters, as described in M. Defrise, F. Noo, H. Kudo, "Improved 2D rebinning of helical cone-beam CT data using John's equation", Proc. 2002 IEEE Nuclear Science and Medical Imaging Symposium, Norfolk (Va.), Paper M10-74, which is hereby incorporated by reference:

$$R^2 g_{u\tilde{q}} - 2ug_a - (R^2+u^2)g_{ua} - Rg_{\alpha a} - uag_{\alpha a} = 0, \quad \text{(equation 10)}$$

where R is the distance from the virtual source position to the iso-center and u is the distance from the central ray to the exposed detector column in fan direction. The line integrals are denoted by g and the derivative of the line integral with respect to a variable is expressed by the index. From the measured line integrals g, the line integrals $g_{\tilde{q}}$ can be extrapolated for a virtual source position $\tilde{g}$ according to $$g(u,a,\alpha,\tilde{q}) = g(u,a,\alpha,0) + \Delta\tilde{q} g_{\tilde{q}}(u,a,\alpha,0). \quad \text{(equation 11)}$$

Therefore, Eq. (10) has to be solved for $\tilde{q}$. Reforming of Eq. (10) to $$g_{u\tilde{q}} = \frac{2u}{R^2}g_a + \frac{(R^2+u^2)}{R^2}g_{ua} + \frac{1}{R}g_{\alpha a} + \frac{ua}{R^2}g_{\alpha a}, \quad \text{(equation 12)}$$

and partial integration with respect to u leads to $$g_{\tilde{q}} = \frac{(R^2+u^2)}{R^2}g_a + \frac{1}{R}\int\left(g_{\alpha a} + \frac{ua}{R}g_{\alpha a}\right)da, \quad \text{(equation 13)}$$

which are the line integrals for the virtual source position $\tilde{q}$.

The acquired and extrapolated data can now be resorted such that it corresponds to an acquisition along a helical trajectory in the x-y-q space. Let $\vec{R}$ be the vector from the center of rotation of the scanning system to the virtual source. The helical trajectory results in:

$$\vec{R}(\alpha) = R \begin{pmatrix} \cos\alpha \\ \sin\alpha \\ k\alpha \end{pmatrix} = R \begin{pmatrix} \cos\alpha \\ \sin\alpha \\ \tilde{q} \end{pmatrix}, \quad \text{(equation 14)}$$

where α denotes the angular source position in relation to the x-axis.

In a certain range, each value of $q \in [q_{min}, q_{max}]$ can be expressed by the linear equation $$q = \tilde{q} + \frac{1}{2hc}\left[\frac{d_{min} + d_{max} - d}{d_{min} \times d_{max}}\right] aE, \quad \text{(equation 15)}$$

which fulfills the data acquisition of a helical trajectory in the x-y-q space. By this description, it is possible to define an offset $\alpha_0$ as a starting point for the helical data acquisition, in order to use redundant data for the reconstruction process. This may lead to better image quality.

The above described steps 1 to 4, in particular Step 3 may be applied and implemented in the CSCT scanner depicted and described with reference to FIGS. 1 to 5, in the scanner depicted in FIG. 6 and in the data processing device depicted in FIG. 13.

As already mentioned above, during the transmission through a material, the x-ray spectrum becomes harder. Due to this, the mean energies of the transmitted x-ray spectra are different depending on the primary spectrum and the material encountered in the object of interest. This causes that when performing a back-projection along the path as set forth in equation 5 on the basis of the different mean energies, different back-projection paths are obtained. According to the present invention it has been found that for contemplating this effect during the reconstruction, the mean energies of the respective back-projection paths have to be obtained. This may be done as set forth in the methods described with reference to FIGS. 10 and 11.

As shown above, the path of the scatter radiation and due to this, the factor β(E) depends on the scatter angle. In the following it is assumed that the attenuation of the scattered radiation is the same as the attenuation of the directly transmitted radiation. The attenuation of the transmitted radiation, i.e. of the primary radiation, may be determined as $$\gamma = \frac{I}{I_0}.$$

This attenuation may be determined by means of the primary radiation detector 15. The application of this assumption causes that the product α(E)×β(E) is independent of the path.

For determining a shift of the mean energies of the scattered photons on the basis of the mean attenuation $$\gamma = \frac{I}{I_0}$$

which has been measured, the following assumptions concerning the material of the object of interest are made. For example, for medical applications it may be assumed that the object of interest primarily consists of water, i.e. that the radiation is primarily transmitted through water. For example, for applications in the field of baggage inspection, a "mean material" may be used consisting, for example, of 10% aluminium and 90% cloth.

In the following, on the basis of the mean attenuation a simulation is performed with respect to the mean energy shift. In other words, it is determined how much the mean energy is shifted up.

For example, for water, an equivalent water thickness may be determined on the basis of a mean attenuation $$\gamma = \frac{I}{I_0}$$

by using the following equation:

$$d = -\frac{\ln(\gamma)}{\mu}.$$

μ is the mean attenuation of the permeated material, i.e. of the water or of the mean material.

FIG. 9 shows a table comprising approximated linear dependencies between energy and a thickness of water and PMMA for a plurality of filtered tungsten spectra. For example, the table of FIG. 9 shows in the first line that when using an x-ray tube with 150 keV and 1.5 mm of Aluminium filter, the mean energy emitted by the tube is 63.3 keV. Assuming an equivalent water thickness of 10 cm, the energy shift would be 7.2 keV. Thus, the mean energy which may be determined at the detector 8 which has been corrected for beam-hardening effects and which has been attenuation corrected is 63.3 keV+7.2 keV=70.5 keV.

Figure 10:
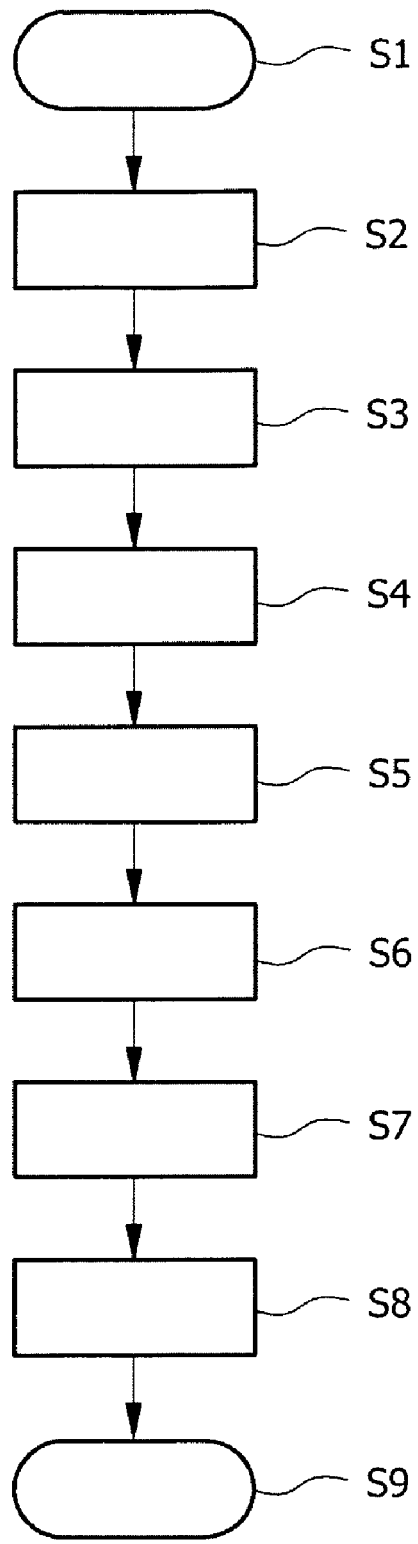
FIG. 10 shows a flow-chart of an exemplary embodiment of a method of operating the computer-tomograph according to the present invention.

FIG. 10 shows a flow-chart of an exemplary embodiment of a method according to the present invention as it may be performed on the CT scanner according to the present invention or the data processing apparatus according to the present invention.

After the start in step S1, an air scan is performed in step S2. An air scan is a scan where no object of interest is in the examination region of the CT scanner. The air scan serves to determine $I_0$. Then, in the subsequent step S3, a mean attenuation γ=

$$\frac{I}{I_0}$$

is determined on the basis of the transmitted radiation, i.e. on the basis of the read outs of the primary radiation detector 15. In other words, a determination of mean attenuation values is performed on the basis of the primary radiation.

Then, in the subsequent step S5 a determination of an equivalent water thickness is performed on the basis of the mean attenuation. This equivalent water thickness (or Lucite thickness (or a thickness of a mean material) may be determined on the basis of the following equation:

$$d = -\frac{\ln(\gamma)}{\mu}.$$

Then, in the subsequent step S6, an energy shift caused by the material is calculated from the equivalent water thickness. This may be done, for example, by referring to a predetermined table such as the table depicted in FIG. 9.

Then, in the subsequent step S7, the initial average energy of the scatter radiation is corrected or compensated by using the energy shift. In other words, in step S7 an attenuation compensation or compensation for beam-hardening effects is performed. Then, in subsequent step S8, a reconstruction is performed by using the corrected energy measurements. The reconstruction may be performed along the back-projection path described above. In other words, the reconstruction may be performed in accordance with steps 1-4 as described above. Then, the method continues to step S9 where it ends.

Figure 11:
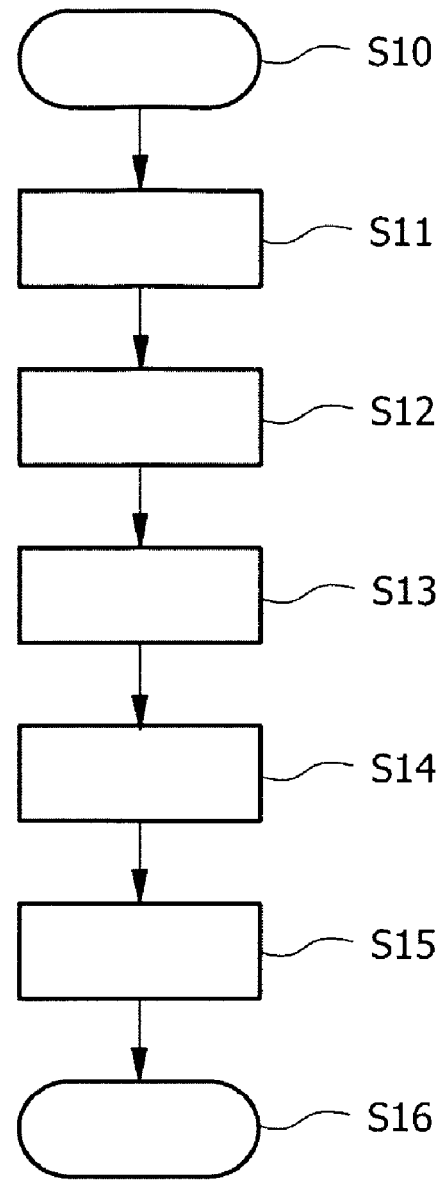
FIG. 11 shows another flow-chart of another exemplary embodiment of a method of operating the computer-tomograph according to the present invention.

FIG. 11 shows another flow-chart of another exemplary embodiment of a method of operating the CT scanner system or data processing apparatus according to the present invention. In contrast to the method described with reference to FIG. 10 where no preliminary CT reconstruction is performed, in the method described with reference to FIG. 11, a CT reconstruction may be performed before the actual reconstruction. Advantageously, this may allow for an improved absorption compensation and/or an improved compensation of beam-hardening effects.

After the start in step S10, an air scan is performed in step S11 for determining $I_0$. Then, in the subsequent step S12, a CT acquisition is performed. In other words, in step S12, a data acquisition of the object volume of interest may be performed, for example, along a helical trajectory. For this, a fan-beam may be used. Advantageously, by using such an arrangement, the projection data of the transmitting as well as of the scattered radiation may be determined at the same time. However, in a variant of this exemplary embodiment of the present invention, a pre-scanning may be performed where only the transmitting radiation is measured, i.e. only the read outs of the primary radiation detector are gathered. Then, a second scan may be performed for determining the scatter radiation.

Then, in the subsequent step S13, from the readouts of the primary radiation detector, i.e. from the transmitted radiation data, a volume data set is reconstructed wherein each voxel comprises an absorption coefficient of the object of interest contained in the object volume of interest. Then, in the subsequent step S14, the absorption compensation and/or compensation of beam-hardening effects is performed. Here, the mean energy for the scattered photons is determined on the basis of the volume data set by taking into account materials of the object of interest occurring on the path of the scattered photons through the object of interest. These materials may be discriminated from the volume data set determined in step S13. For example, these materials may be discriminated by performing suitable thresholding operations.

In other words, since the projection path of the object is known for a scattered photon, for a known spectrum, the attenuation along this path is calculated. By performing suitable thresholding operations, materials along the scatter path of the respective photon may be identified and the absorption spectra thereof may be taken into account. From the resulting spectra, a mean energy may be determined for the scattered photon.

Then, in the subsequent step S15, a reconstruction may be performed by using these mean energies. Due to this, during the actual reconstruction performed in step S15, where the scatter function is determined for each voxel, the mean energy determined in step S14 is used in equation 5 and thus may allow for improved spectral resolution of the reconstructed scatter function in dependence of the wave vector transfer.

Furthermore, on the basis of the absorption values determined in step S13, an absorption correction may be performed for the respective projection path which also may allow for an improved image quality. Then, the method continues to step S16 where it ends.

Figure 12:
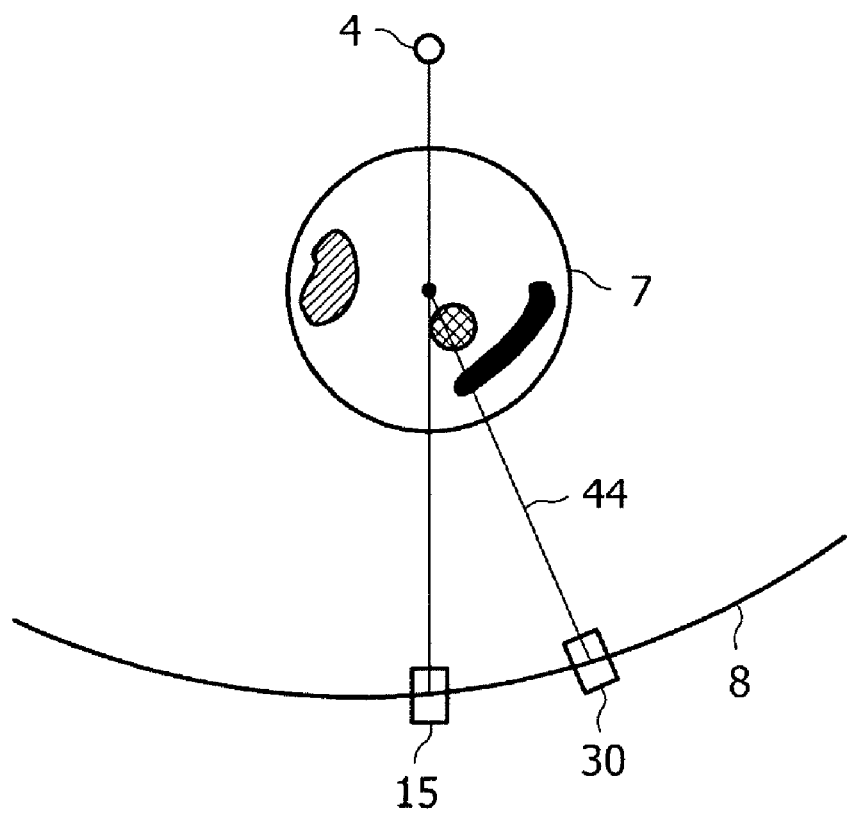
FIG. 12 is a simplified schematic representation of a scatter event for further explaining the method depicted in FIG. 11.

FIG. 12 shows a simplified schematic representation for further explaining the method described with reference to FIG. 11. As may be taken from FIG. 12, a radiation emitted by the source of radiation 4 is transmitted through the object of interest 7 and may be measured by means of the primary radiation detector comprising line 15. The scatter radiation scattered from the object of interest 7 may be determined by means of the scatter radiation detector 30.

In a preliminary step, a CT reconstruction on the basis of the read outs of the detector line 15, i.e. of the primary radiation detector, is performed. From this, a volume data set is reconstructed. From the volume data set, materials which are encountered by the scatter radiation 44 on its path through the object of interest 7 may be determined. The beam-hardening effect caused by these materials may be taken into account and also the absorption spectra caused by these materials may be taken into account to correct the energy actually measured by detector line 30.

Figure 13:
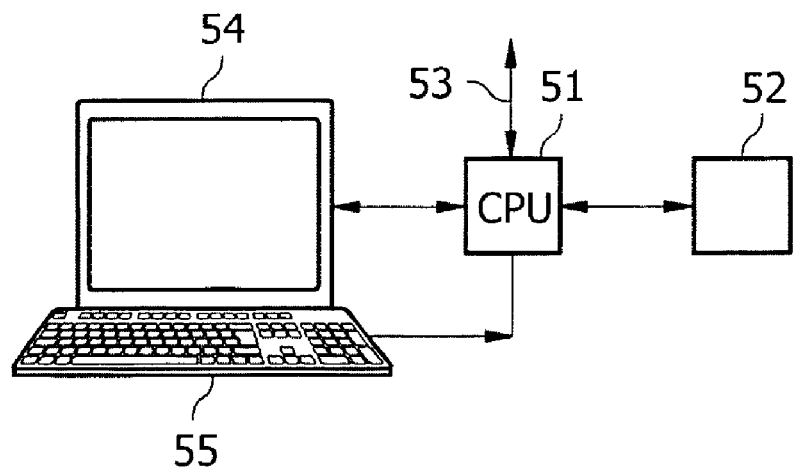
FIG. 13 shows a simplified schematic representation of an exemplary embodiment of a data processing device according to the present invention adapted to perform the methods of the present invention.

FIG. 13 shows an exemplary embodiment of a data processing device for performing the methods of the present invention, for example, the methods described with reference to FIGS. 10 and 11. As may be taken from FIG. 9, a central processing unit (CPU) or image processor 51 is connected to a memory 52 for storing read outs from the detectors or the finally reconstructed data. As indicated before, the data may be acquired by a CSCT scanner as depicted in FIGS. 1 and 6. The data processor 51 may furthermore be connected to a plurality of input/output-network or other diagnosis devices. The image processor 51 is furthermore connected to a display 54 (for example to a computer monitor) for displaying information or images computed or adapted in the image processor 51. An operator may interact with the data processor 51 via a keyboard 55 and/or other input or output devices which are not depicted in FIG. 1.

The present invention described above may, for example, be applied in the field of medical imaging. However, as described above, the present invention may also be applied in the field of non-destructive testing or baggage inspection. Advantageously, the present invention may allow for a very good spectra resolution of reconstructed scatter functions, for example in order to discriminate materials having the same attenuation values. Furthermore, an improved image quality in particular for medical applications may be achieved. The present invention may be applied as add-on functionality for cone-beam CT systems. Preferably, the present invention is applied in conjunction with non-energy resolving detectors.

The invention claimed is:

1. A method of reconstructing coherent scatter computed tomography data of an object of interest, the method comprising the acts of:
   acquiring attenuation data of the object of interest from primary radiation transmitted through the object of interest;
   performing a beam hardening compensation of scatter radiation data based on the acquired attenuation data and based on an energy shift of an equivalent object equivalent to the object of interest; wherein the scatter radiation data is based on scatter radiation scattered from the object of interest; and
   reconstructing the coherent scatter computed tomography data by using the compensated scatter radiation data.

2. The method of claim 1, wherein the energy shift of the equivalent object caused by a beam hardening effect is known.

3. The method of claim 1, further comprising the acts of:
determining a mean attenuation caused by the object of interest based on the attenuation data;
determining an equivalent thickness of a pre-selected material of the equivalent object based on the mean attenuation;
determining the energy shift based on the equivalent thickness of the pre-selected material; and
compensating the scatter radiation data by using the energy shift.

4. The method of claim 1, further comprising the acts of:
reconstructing a volume data set comprising absorption coefficients of the object of interest;
determining radiation spectra for scattered photons of the scatter radiation;
determining mean energies of the scattered photons based on the radiation spectra; and
performing a reconstruction of the coherent scatter computed tomography data by using the mean energies.

5. The method of claim 1, further comprising the acts of determining, based on the attenuation data, a material which is located on a path of a scattered photon of the scatter radiation in the object of interest;
determining a mean energy of the scattered photon using an absorption spectrum of the material; and
using the mean energy for the reconstruction.

6. The method of claim 1, wherein the performing act includes correcting energy of the scatter radiation by the energy shift of the equivalent object.

7. A coherent scatter computed tomography apparatus, the apparatus comprising:
a detector assembly with a source of radiation,
a first detector; and
a second detector;
wherein the detector assembly is arranged for rotation around an object of interest;
wherein the first detector and the second detector are arranged opposite to the source of radiation;
wherein the first detector is arranged for acquiring attenuation data of the object of interest from primary radiation transmitted through the object of interest;
wherein the second detector is arranged for acquiring scatter radiation data of the object of interest from scatter radiation scattered from the object of interest;
wherein the apparatus performs a beam hardening compensation of the scatter radiation data based on the acquired attenuation data and based on an energy shift of an equivalent object equivalent to the object of interest; and
wherein the apparatus performs a reconstruction of coherent scatter computed tomography data by using the compensated scatter radiation data.

8. The apparatus of claim 7, wherein the beam hardening compensation is performed based on an energy shift determined based on an equivalent object having a known beam hardening effect.

9. The apparatus of claim 7, wherein, based on the attenuation data, a material is determined which is located on a path of a scattered photon of the scatter radiation in the object of interest; wherein an absorption spectrum of the material is used for determining a mean energy of the scattered photon; and wherein the mean energy is used for the reconstruction.

10. The coherent scatter computed tomography apparatus of claim 7, wherein the beam hardening compensation includes correcting energy of the scatter radiation by the energy shift of the equivalent object.

11. A data processing device for reconstructing coherent scatter computed tomography data of an object of interest, wherein the device comprises:
a memory for storing attenuation data and scatter radiation data; and
a data processor adapted to perform the following acts:
acquiring attenuation data of the object of interest from primary radiation transmitted through the object of interest;
performing a beam hardening compensation of scatter radiation data based on the acquired attenuation data and based on an energy shift of an equivalent object equivalent to the object of interest;
wherein the scatter radiation data is based on scatter radiation scattered from the object of interest; and
reconstructing the coherent scatter computed tomography data by using the compensated scatter radiation data.

12. The data processing device of claim 11, wherein the performing act includes correcting energy of the scatter radiation by the energy shift of the equivalent object.

13. A computer readable medium embodying a computer program for reconstructing coherent scatter computed tomography data of an object of interest, wherein, when the computer program is executed on one of a data processor and a coherent scatter computed tomography apparatus, the following acts are executed:
acquiring attenuation data of the object of interest from primary radiation transmitted through the object of interest;
performing a beam hardening compensation of scatter radiation data based on the acquired attenuation data and based on an energy shift of an equivalent object equivalent to the object of interest;
wherein the scatter radiation data is based on scatter radiation scattered from the object of interest; and
reconstructing the coherent scatter computed tomography data by using the compensated scatter radiation data.

14. The computer readable medium of claim 13, wherein the performing act includes correcting energy of the scatter radiation by the energy shift of the equivalent object.

* * * * *